United States Patent
Luyken

(10) Patent No.: US 11,492,324 B2
(45) Date of Patent: Nov. 8, 2022

(54) METHOD FOR THE PRODUCTION OF ETHYLENEAMINES

(71) Applicant: BASF SE, Ludwigshafen am Rhein (DE)

(72) Inventor: Hermann Luyken, Ludwigshafen am Rhein (DE)

(73) Assignee: BASF SE, Ludwigshafen am Rhein (DE)

(*) Notice: Subject to any disclaimer, the term of this patent is extended or adjusted under 35 U.S.C. 154(b) by 249 days.

(21) Appl. No.: 16/759,428

(22) PCT Filed: Oct. 17, 2018

(86) PCT No.: PCT/EP2018/078326
§ 371 (c)(1),
(2) Date: Apr. 27, 2020

(87) PCT Pub. No.: WO2019/081286
PCT Pub. Date: May 2, 2019

(65) Prior Publication Data
US 2021/0371372 A1 Dec. 2, 2021

(30) Foreign Application Priority Data
Oct. 27, 2017 (EP) .................................. 17198933

(51) Int. Cl.
*C07C 209/84* (2006.01)
(52) U.S. Cl.
CPC .................. *C07C 209/84* (2013.01)
(58) Field of Classification Search
None
See application file for complete search history.

(56) References Cited

U.S. PATENT DOCUMENTS

| 2,519,803 A | 8/1950 | George et al. |
| 2,861,995 A | 11/1958 | Mackenzie |

(Continued)

FOREIGN PATENT DOCUMENTS

| CN | 102190588 A | 9/2011 |
| CN | 102233272 A | 11/2011 |

(Continued)

OTHER PUBLICATIONS

International Preliminary Report on Patentability received for PCT Patent Application No. PCT/EP2018/078326, dated Sep. 20, 2019, 12 pages (5 pages of English Translation and 7 pages of Original Document).
International Search Report and Written Opinion received for PCT Patent Application No. PCT/EP2018/078326, dated Dec. 7, 2018, 9 pages (2 pages of English Translation and 7 pages of Original Document).

*Primary Examiner* — Sudhakar Katakam
*Assistant Examiner* — Jennifer C Sawyer
(74) *Attorney, Agent, or Firm* — Faegre Drinker Biddle & Reath LLP

(57) ABSTRACT

The present invention relates to a process for purifying ethylenediamine, in which a) a mixture comprising water (H2O), ethylenediamine (EDA) and N-methylethylenediamine (NMEDA) is introduced into a rectification column (NMEDA removal column), where the mixture introduced comprises at least the amount of water as required for the formation of a high-boiling azeotrope of EDA and water at the appropriate bottom temperature; and the EDA-comprising bottom product from the NMEDA removal column is introduced into a second rectification column (EDA dewatering column), wherein the pressure at the top of the EDA dewatering column is adjusted such that the boiling temperature of the mixture obtained at the top is 10° C. or higher than the bottom temperature of the NMEDA removal column, which comprises (i) partly or fully condensing the vapors from the top of the EDA dewatering column in a (Continued)

condenser which is cooled with a medium which is at least partly evaporated during the condensation and the vapor thus formed is used at least partly to heat the evaporator of the NMEDA removal column; and/or (ii) introducing the vapors from the top of the EDA dewatering column into the NMEDA removal column.

15 Claims, 4 Drawing Sheets

(56) References Cited

U.S. PATENT DOCUMENTS

| | | | |
|---|---|---|---|
| 3,112,318 | A | 11/1963 | Lemon et al. |
| 3,137,730 | A | 6/1964 | Fitz-William |
| 4,111,840 | A | 9/1978 | Best |
| 2012/0253077 | A1* | 10/2012 | Jodecke ............ C07C 209/84 203/91 |

FOREIGN PATENT DOCUMENTS

| | | |
|---|---|---|
| DE | 1154121 B | 9/1963 |
| DE | 1172268 B | 6/1964 |
| EP | 0234680 A1 | 9/1987 |
| EP | 2346809 A1 | 7/2011 |
| EP | 2487151 A1 | 8/2012 |
| EP | 2507202 A1 | 10/2012 |
| GB | 1027508 A | 4/1966 |
| WO | 2007/093514 A1 | 8/2007 |
| WO | 2008/104552 A1 | 9/2008 |
| WO | 2008/104582 A2 | 9/2008 |
| WO | 2008/104592 A1 | 9/2008 |
| WO | 2010/042158 A1 | 4/2010 |
| WO | 2011/067226 A1 | 6/2011 |
| WO | 2015/135971 A1 | 9/2015 |

* cited by examiner

METHOD FOR THE PRODUCTION OF ETHYLENEAMINES

CROSS-REFERENCE TO RELATED APPLICATIONS

This application is a national stage application (under 35 U.S.C. § 371) of PCT/EP2018/078326, filed Oct. 17, 2018, which claims benefit of European Application No. 17198933.8, filed Oct. 27, 2017, both of which are incorporated herein by reference in their entirety.

The present invention relates to a process for purifying ethylenediamine (EDA).

Ethylenediamine is used predominantly as an intermediate for the production of bleach activators, crop protection agents, pharmaceuticals, lubricants, textile resins, polyamides, paper auxiliaries, gasoline additives and many other substances.

There are numerous known processes for preparing EDA (see, for example, Ullmann's Encyclopedia of Industrial Chemistry, "Amines Aliphatic", section 8.1.1. DOI: 10.1002/1436007.a02_001).

In the preparation of ethylenediamine, N-methylethylenediamine (NMEDA) can be formed by side reactions.

For example, in the reaction of monoethanolamine (MEA) with ammonia to give EDA, a degradation reaction of monoethanolamine can directly give rise to carbon monoxide (CO) and methylamine (decarbonylation). The methylamine can in turn react directly with further monoethanolamine to give NMEDA.

NMEDA can also form in the dimerization of monoethanolamine to aminoethanolamine (AEEA) when AEEA is degraded directly by decarbonylation to NMEDA.

NMEDA can also form in the preparation of EDA from C1 units such as hydrogen cyanide and formaldehyde.

As well as NMEDA, poly-N-methylated ethylenediamines can also form, for example bis(N-methyl-1,2-ethanediamine). In terms of amount, however, the formation of NMEDA is typically dominant.

For most industrial applications, the market demands a purity for EDA of at least 99.5% by weight. Organic secondary components, including NMEDA, may be present with a proportion of not more than 0.5% by weight. Furthermore, the water content may be not more than 0.5% by weight.

More particularly, in many industrial applications, a purity of EDA is specified where the proportion of NMEDA is below 1000 ppm by weight.

EDA which, as a result of its preparation, has a higher NMEDA content has to be worked up correspondingly, so as to obtain EDA that has the required specifications.

EP2487151 presents a process for depleting alkylethyleneamines from ethyleneamine mixtures, wherein a mixture consisting of ethylenediamine, water and one or more alkylethylenediamines is subjected to such conditions that an azeotrope is formed between the water and the alkylethyleneamines, which is separated from the remaining composition. It is disclosed that the pressure in the rectification column in which the azeotrope of water and alkylethylenediamine is separated off is in the range from 1.01 to 2.12 bar, preferably 1.5 to 1.98 bar. In example 1, the distillation is effected at a top pressure of 1.634 bar, a top temperature of 115° C. and a bottom temperature of 176° C. Apart from these technical details relating to the distillation, the disclosure does not contain any further technical information as to which measures the person skilled in the art has to take in order that an azeotrope of alkylethyleneamine and water is formed.

A further process for separating NMEDA from EDA is disclosed in EP2507202. This disclosure teaches that the removal of NMEDA is effected in a rectification column at a column top pressure in the range from 0.01 bar to 4 bar and that the mixture to be distilled comprises at least a sufficient amount of water that the condition $H=a*X/Y$ is fulfilled, where H is the proportion by weight of water in the mixture to be distilled, X is the proportion by weight of water and Y is the proportion by weight of EDA at the azeotropic point of a binary mixture of water and EDA at the column pressure in question, and a is a real number having a value of 0.9 or more.

It was an object of the present invention to provide a process for purifying an EDA comprising NMEDA so as to achieve an on-spec EDA having a low NMEDA content, preferably an NMEDA content of 1000 ppm by weight or less. In addition, the energy demand in the distillation was to be reduced, such that the purification can be effected under economically favorable conditions.

The object of the present invention was also achieved by a process for purifying ethylenediamine, in which
a) a mixture comprising water ($H_2O$), ethylenediamine (EDA) and N-methylethylenediamine (NMEDA) is introduced into a rectification column (NMEDA removal column), where the mixture introduced comprises at least the amount of water as required for the formation of a high-boiling azeotrope of EDA and water at the appropriate bottom temperature; and
b) the EDA-comprising bottom product from the NMEDA removal column is introduced into a second rectification column (EDA dewatering column),
which comprises (i) partly or fully condensing the vapors from the top of the EDA dewatering column in a condenser which is cooled with a medium which is at least partly evaporated during the condensation and the vapor thus formed is used at least partly to heat the evaporator of the NMEDA removal column; and/or (ii) introducing the vapors from the top of the EDA dewatering column into the NMEDA removal column.

It has been found that, surprisingly, the thermal energy from the vapors from the EDA dewatering column can be used in a suitable manner to reduce the energy demand in the evaporation in the NMEDA removal column. This created a particularly energy-efficient purification process.

The following abbreviations are used hereinafter:
AEEA: aminoethylethanolamine
AEP: aminoethylpiperazine
DETA: diethylenetriamine
EDA: ethylenediamine
EDC: ethylene dichloride
HEP: hydroxyethylpiperazine
HPA: heavy polyamines
MEA: monoethanolamine
MEG: monoethylene glycol
NMEDA: N-methylethylenediamine
PEHA: pentaethylenehexamines
PIP: piperazine
TEPA: tetraethylenepentamine
TETA: triethylenetetramine Unless specified otherwise, pressure figures relate to the absolute pressure figure.

A BRIEF DESCRIPTION OF THE FIGURES

Mixtures

Figure 1:
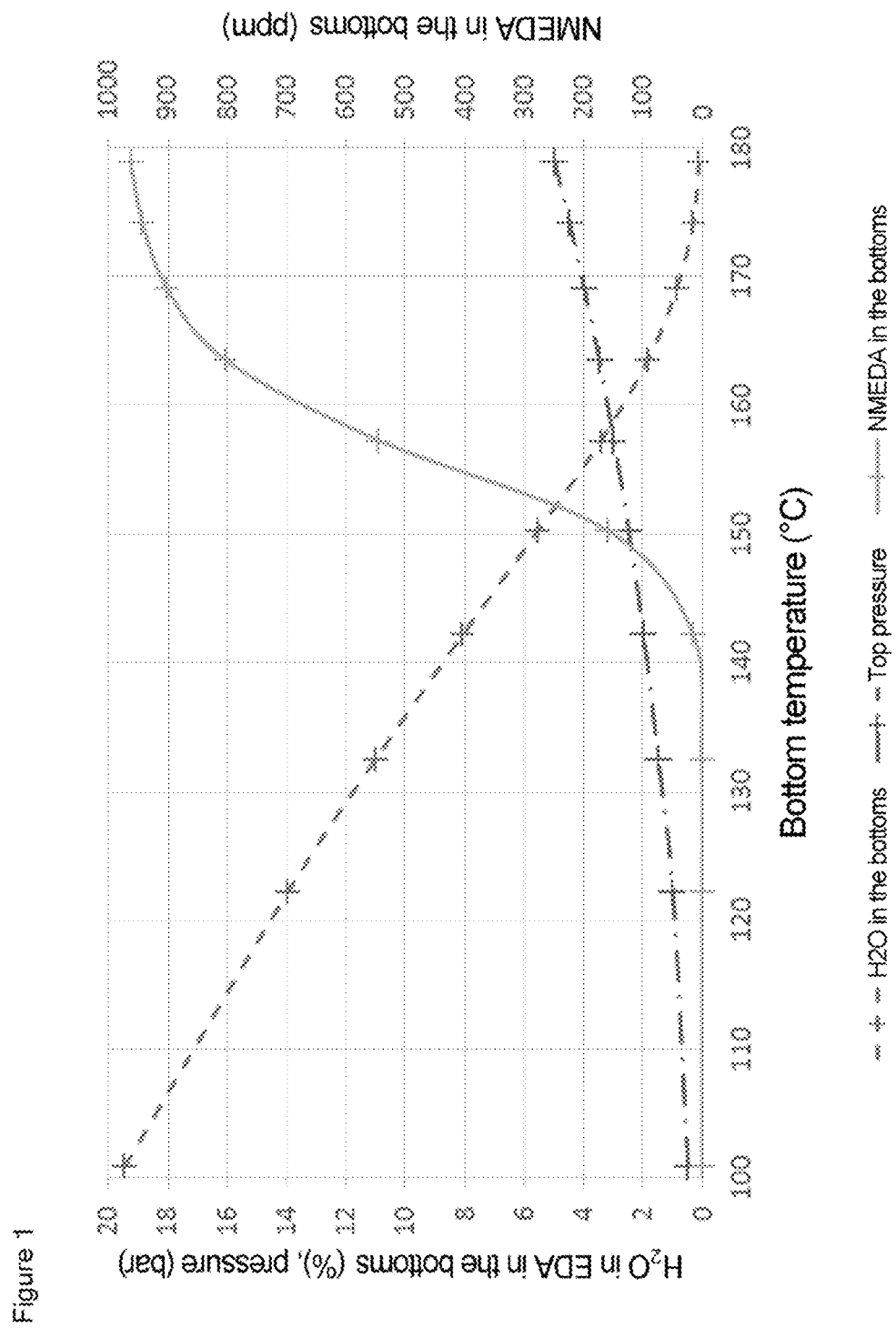
FIG. 1 illustrates the results as a graph from example 1.

According to the invention, mixtures comprising NMEDA, EDA and water are used in the process for purifying EDA.

Preparation of the Mixtures

Such mixtures can be prepared by first conducting an EDA preparation process. After the EDA preparation process, ammonia is generally removed, which can also include the removal of hydrogen.

In the preferred embodiment, the reaction output obtained from the ammonia removal is used directly in the process of the invention without further workup steps.

In a further embodiment, it is possible to use a mixture comprising NMEDA, EDA and water, which is obtainable by complete or partial removal of the higher-boiling amines (removal of the higher-boiling amines) after the removal of ammonia.

EDA Preparation Process

The first stage for preparation of the mixtures which can be used in the process of the invention is typically an EDA preparation process.

EDA can be prepared by various processes.

In a preferred embodiment (MEA process), EDA is prepared by reaction of MEA with NH3.

In a further preferred embodiment (C1 process), EDA is prepared by reaction of formaldehyde, hydrogen cyanide, ammonia and hydrogen.

In a further preferred embodiment (EDC process), EDA is prepared by reaction of ethylene dichloride with ammonia (EDC process).

In yet a further preferred embodiment (MEG process), EDA can be prepared by reaction of MEG with ammonia.

MEA Process

The reaction of MEA and ammonia is described, for example, in U.S. Pat. No. 2,861,995, DE-A-1 172 268 and U.S. Pat. No. 3,112,318. An overview of the various process variants of the reaction of MEA with ammonia can be found, for example, in the PERP Report No. 138 "Alkyl-Amines", SRI International, March 1981 (especially pages 81-99, 117).

The reaction of monoethanolamine with ammonia is preferably conducted in a fixed bed reactor over a transition metal catalyst at 150-250 bar and 160-210° C. or over a zeolite catalyst at 1-20 bar and 280-380° C.

Transition metal catalysts used with preference comprise Ni, Co, Cu, Ru, Re, Rh, Pd or Pt or a mixture of two or more of these metals on an oxidic support (e.g. $Al_2O_3$, $TiO_2$, $ZrO_2$, $SiO_2$). Preferred zeolite catalysts are mordenites, faujasites and chabazites.

To achieve a maximum EDA selectivity, in the case of transition metal catalysis, a molar ratio of ammonia to monoethanolamine of 6-20, preferably 8-15, is generally employed, and, in the case of zeolite catalysis, generally 20-80, preferably 30-50.

The MEA conversion is generally kept between 10% and 80%, preferably 40-60%.

In continuous operation, preferably, a catalyst space velocity in the range of 0.3-0.6 kg/(kg*h) (kg MEA per kg cat. per hour) is established.

To maintain the catalyst activity, when metal catalysts are used, preference is given to additionally running 0.05-0.5% by weight (based on the MEA+$NH_3$+$H_2$ reaction input) of hydrogen into the reactor.

C1 Process

A reaction output can also be prepared by the reaction of formaldehyde, hydrogen cyanide, ammonia and hydrogen.

For instance, U.S. Pat. No. 2,519,803 describes a process for preparing ethylenediamine by the hydrogenation of a partly purified aqueous reaction mixture which results from an amination of formaldehyde cyanohydrin (FACH) and comprises aminoacetonitrile as intermediate.

Formaldehyde cyanohydrin can in turn be obtained by reaction of formaldehyde with hydrogen cyanide. A process description for preparation of FACH can be found, for example, in application PCT/EP2008/052337, page 26, and in application WO-A1-2008/104582, page 30 (variants a) and b)), to which reference is made explicitly here.

DE-A 1 154 121 relates to a further process for preparing ethylenediamine, wherein the hydrogen cyanide, formaldehyde, ammonia and hydrogen reactants are reacted in the presence of a catalyst in a "one-pot" process.

WO-A1-2008/104592 relates to a process for preparing EDA by hydrogenation of aminoacetonitrile. Aminoacetonitrile is typically obtained by reaction of formaldehyde cyanohydrin with ammonia, where formaldehyde cyanohydrin is in turn generally prepared from hydrogen cyanide and ammonia.

Preferably, a reaction output comprising EDA and NMEDA is prepared by the process described in WO-A-2008/104592, to which reference is hereby made explicitly.

EDC Process

EDA can also be prepared by reaction of ethylene dichloride with ammonia (EDC process). The reaction of EDC with ammonia is described, for example, in EP 2346809, in the abovementioned PERP Report and in the references cited therein.

MEG Process

In a further embodiment, EDA can be prepared by reaction of MEG with ammonia. The reaction of MEG with ammonia can be effected in the liquid phase or the gas phase. Gas phase reactions are disclosed, for example, in CN 102190588 and CN 102233272, while reactions in the liquid phase are disclosed, for example, in U.S. Pat. Nos. 4,111, 840, 3,137,730, DE 1 72 268 and WO 2007/093514.

Composition of the Reaction Outputs from the EDA Preparation Processes

The mixtures that are prepared by the abovementioned preparation processes comprise, as well as EDA, NMEDA and water, according to the preparation method, generally also hydrogen;

ammonia;

higher-boiling amines;

ethylene glycol (MEG); and organic by-products.

Higher-boiling amines refer hereinafter to acyclic and cyclic compounds that comprise 2 or more amine groups (primary, secondary or tertiary) or that comprise one or more amine groups and one or more OH groups, and that have a higher boiling point than EDA at the same pressure, for example piperazine (PIP), monoethanolamine (MEA), diethylenetriamine (DETA), aminoethylethanolamine (AEEA), triethylenetetramine (TETA) and higher ethyleneamines (higher ethyleneamines refer hereinafter to those higher-boiling ethyleneamines having a higher boiling point than TETA, e.g TEPA).

Organic by-products refer hereinafter to all unconverted starting materials and reaction products that are not higher-boiling amines, MEG, water, hydrogen, ammonia or NMEDA.

Ammonia Removal

The mixtures from the abovementioned preparation processes generally comprise ammonia.

The amount of ammonia in the reaction outputs is typically in the range from 50% to 90% by weight, more preferably in the range from 60% to 85% by weight and most preferably in the range from 70 to 80% by weight.

Before the reaction outputs are used in the process of the invention, hydrogen and ammonia are typically separated from the mixtures obtained by the abovementioned preparation processes.

Hydrogen and ammonia can be separated from the reaction mixture by methods known to those skilled in the art.

Preferably, the removal of ammonia and hydrogen is conducted by distillation or rectification.

This can be effected in distillation stills or rectification columns.

In the case of rectification, it is possible to use columns having a rectifying section and stripping section.

If the depletion of secondary components such as methylamine from the ammonia is required, the use of a rectifying section is advantageous.

Preference is given to using columns without a rectifying section since no reflux is required in that case, which reduces the energy demand of rectification.

The removal of hydrogen and ammonia can be conducted in a single stage at a particular pressure or in a staged manner in a series of setups in which the pressure is varied in order to match top and bottom temperatures such that they are practicable.

Preferably, the pressure and composition at the top and bottom are chosen such that the condensation temperature is higher than 20° C., more preferably higher than 30° C., most preferably higher than 35° C. If the condensation temperature is within the ranges mentioned, the condenser can be cooled with cooling water which is generally at a temperature of 20-80° C., preferably 30 to 70° C. and more preferably 35-50° C.

The bottom temperature is preferably less than 250° C., more preferably less than 220° C., most preferably less than 200° C.

While the setting of the pressure is crucial for the setting of the temperatures, the temperatures in the distillation are also affected by setting of a particular concentration. For instance, it is possible to increase the condensation temperature at the top by drawing off not only ammonia but also other components having a higher boiling point than ammonia, for example water, overhead as well. In this case, it is advantageous to operate the condenser in backmixed mode (called "closed condensation" by the person skilled in the art), such that the condensation takes place within a narrow temperature range. A suitable condenser for this type of condensation is one in which the condensation takes place in cocurrent with the outflow of the condensate, or a direct condenser in which cold liquid which is pumped in circulation is brought into contact with the vapors to be condensed.

Preferably, in a first stage, the majority of ammonia is distilled off at high pressure, for example higher than 10 bar, preferably higher than 15 bar, more preferably higher than 20 bar, while still permitting a particular ammonia concentration in the bottom, with which the desired bottom temperature is established. The hydrogen present in the reaction output is likewise removed overhead. Preferably, in a first condenser, the majority of the ammonia is condensed out of the vapors at a relatively high temperature. Hydrogen is enriched here in the gas phase in accordance with the dew point curve of the mixture. Since complete condensation of the mixture is not possible at standard ambient temperatures, this gives rise to a gaseous output in the condenser. The latter can be introduced into a second condenser in which the temperature can be lowered further by cooling with a colder coolant, such that ammonia is further depleted from the gas phase and a second offgas with lower ammonia content is formed. The offgas from the first or second condenser can also be treated by scrubbing in order to recover the majority of the ammonia present therein. This can be effected by use of standard methods known to those skilled in the art, such as scrubbing columns or Venturi scrubbers. This involves contacting the offgas with a preferably cooled liquid having a higher boiling point than ammonia, preferably water. In a particularly preferred variant, the scrubbing water is taken from another stage in the same process. This affords an ammonia-enriched liquid stream and an ammonia-depleted offgas which generally comprises hydrogen removed. This offgas can be sent to incineration or recycled into an EDA production process. More preferably, the ammonia-enriched stream is recycled into the ammonia removal, for example the stage into which the reaction output is introduced.

Further preferably, the ammonia-containing bottoms output from the first stage of the ammonia removal is guided into a second stage which is operated at a lower pressure than the first stage. The pressure in the second stage is adjusted such that the desired bottom temperature is established, with ammonia being present only in a low concentration, if at all, in the bottoms output from the second stage. The condensation temperature at the top of the second stage is adjusted by entrainment of a component having a higher boiling point than ammonia, preferably water, such that the resulting mixture can be condensed with the desired coolant, for example river water or ambient air. In a particularly preferred variant, the ammonia-comprising mixture drawn off overhead is recycled into the first stage.

It is also possible to subdivide the hydrogen and ammonia removal into a further (zeroth) stage which precedes the first stage and is operated at the same pressure but at a lower bottom temperature than the first stage, such that some of the ammonia can be evaporated at a lower temperature. In this way, cheaper energy at lower temperature, for example waste heat, can be used to save on energy costs. Preferably, the vapors from the zeroth stage are condensed in the same condenser as the vapors from the first stage.

Composition of the Output from the Ammonia Removal

After the removal of ammonia and optionally hydrogen, a mixture comprising not only water, EDA and NMEDA but generally also higher-boiling amines and organic by-products is obtained.

After the removal of NH3 and optionally hydrogen, the output from the hydrogen/ammonia removal can be used directly in the process of the invention.

The mixture obtained after the removal of ammonia, which can be used in the process of the invention, comprises preferably 20% to 75% by weight of EDA, more preferably 30% to 65% by weight of EDA and most preferably 35% to 60% by weight of EDA.

The weight ratio of EDA to NMEDA is preferably 1:0.0005 (500 ppm by weight of NMEDA) to 1:0.2 (200 000 ppm by weight of NMEDA), more preferably 1:0.001 (1000 ppm by weight) to 1:0.05 (50 000 ppm by weight of NMEDA) and most preferably 1:0.005 (5000 ppm by weight of NMEDA) to 1:0.01 (10 000 ppm by weight of NMEDA).

The proportion of ammonia is preferably less than 5% by weight of ammonia, more preferably less than 2% by weight of ammonia, more preferably less than 1% by weight of ammonia and especially preferably less than 0.5% by weight.

The proportion of higher-boiling amines and other high boilers such as MEG is preferably in the range from 5% to 90% by weight, more preferably in the range from 30% to 85% by weight and most preferably in the range from 40% to 70% by weight.

In a preferred embodiment, the weight ratio of the abovementioned components in the mixture used in the process is preferably:
EDA:NMEDA=1:0.0005 to 0.2;
EDA:ammonia=1:0 to 0.05;
EDA:higher-boiling amines=1:0 to 2.0; and
EDA:organic by-products=1:0 to 0.05;
and more preferably:
EDA:NMEDA=1:0.001 to 0.05;
EDA:ammonia=1:0 to 0.025;
EDA:higher-boiling amines=1:0.05 to 1; and
EDA:organic by-products=1:0.0001 to 0.025; and
most preferably
EDA:NMEDA=1:0.005 to 0.01;
EDA:ammonia=1:0 to 0.025;
EDA:higher-boiling amines=1:0.05 to 1; and
EDA:organic by-products=1:0.0001 to 0.025.

In a further preferred embodiment, EDA is prepared by reaction of MEG and NH3. In this further particularly preferred embodiment, the weight ratio of the abovementioned components in the mixture used in the process is preferably:
EDA:NMEDA=1:0.0005 to 0.2;
EDA:ammonia=1:0 to 0.05;
EDA:higher-boiling amines=1:0 to 2.0; and
EDA:MEG=1:0.5 to 10.0
EDA:organic by-products=1:0 to 0.05;
and more preferably:
EDA:NMEDA=1:0.001 to 0.05;
EDA:ammonia=1:0 to 0.025;
EDA:higher-boiling amines=1:0.05 to 1; and
EDA:MEG=1:1.0 to 8.0
EDA:organic by-products=1:0.0001 to 0.025; and
most preferably
EDA:NMEDA=1:0.005 to 0.01;
EDA:ammonia=1:0 to 0.025;
EDA:higher-boiling amines=1:0.05 to 1; and
EDA:MEG=1:2.0 to 5.0
EDA:organic by-products=1:0.0001 to 0.025.

The mixtures obtained after the removal of ammonia can be used directly in the process of the invention.

Removal of the Higher-Boiling Amines

As an alternative to the direct use of the mixture from the removal of ammonia, after the removal of ammonia, it is possible to partially or completely remove the higher-boiling amines and other high boilers, for example MEG.

In a preferred embodiment, after the removal of ammonia, all higher-boiling amines (including PIP) are removed.

This is preferably effected in a rectification column which is operated in such a way that the higher-boiling amines are obtained in the lower part of the column, preferably in the bottom of the column, and a mixture comprising water, NMEDA and EDA is drawn off in the upper region of the columns, preferably at the top of the column.

The exact operating conditions of the rectification column can, in accordance with the separation performance of the column used, be determined in a routine manner by the person skilled in the art by customary calculation methods using the known vapor pressures and evaporation equilibria of the components introduced into the rectification column.

At the top of the column, a mixture that can be used in the process of the invention for removal of NMEDA and EDA is obtained.

In a further preferred embodiment, all higher-boiling amines and other high boilers, for example MEG, apart from PIP are removed.

This is preferably effected in a rectification column which is operated in such a way that the higher-boiling amines apart from PIP are obtained in the lower part of the column, preferably in the bottom of the column, and a mixture comprising water, NMEDA, EDA and PIP is drawn off in the upper region of the columns, preferably at the top of the column.

The exact operating conditions of the rectification column can, in accordance with the separation performance of the column used, be determined in a routine manner by the person skilled in the art by customary calculation methods using the known vapor pressures and evaporation equilibria of the components introduced into the rectification column.

At the top of the column, a mixture that can be used in the process of the invention for removal of NMEDA and EDA is obtained.

Composition of the Mixtures after Removal of the Higher-Boiling Amines

In an embodiment in which the higher-boiling amines and other high boilers, for example MEG, are partially or completely removed, the weight ratio of the abovementioned components in the mixture used in the process is preferably:
EDA:NMEDA=1:0.0005 to 0.2;
EDA:ammonia=1:0 to 0.05;
EDA:PIP=1:0 to 0.05
EDA:higher-boiling amines=1:0 to 0.1 and
EDA:MEG=1:0 to 0.1
EDA:organic by-products=1:0 to 0.05;
and more preferably:
EDA:NMEDA=1:0.001 to 0.05;
EDA:PIP=1:0 to 0.02;
EDA:ammonia=1:0 to 0.025;
EDA:higher-boiling amines=1:0 to 0.05; and
EDA:MEG=1:0 to 0.05
EDA:organic by-products=1:0.0001 to 0.025; and
most preferably
EDA:NMEDA=1:0.005 to 0.01;
EDA:ammonia=1:0 to 0.025;
EDA:PIP=1:0 to 0.01
EDA:higher-boiling amines=1:0 to 0.02; and
EDA:MEG=1:0 to 0.001
EDA:organic by-products=1:0.0001 to 0.025.

In an embodiment in which the higher-boiling amines and other high boilers, for example MEG, apart from PIP are partially or completely removed, the weight ratio of the abovementioned components in the mixture used in the process is preferably:
EDA:NMEDA=1:0.0005 to 0.2;
EDA:ammonia=1:0 to 0.05;

EDA:PIP=1:0.1 to 2
EDA:higher-boiling amines=1:0 to 0.1 and
EDA:MEG=1:0 to 0.1
EDA:organic by-products=1:0 to 0.05;
and more preferably:
EDA:NMEDA=1:0.001 to 0.05;
EDA:PIP=1:0.2 to 1;
EDA:ammonia=1:0 to 0.025;
EDA:higher-boiling amines=1:0 to 0.05; and
EDA:MEG=1:0 to 0.05
EDA:organic by-products=1:0.0001 to 0.025; and
most preferably
EDA:NMEDA=1:0.005 to 0.01;
EDA:ammonia=1:0 to 0.025;
EDA:PIP=1:0.3 to 0.5
EDA:higher-boiling amines=1:0 to 0.02; and
EDA:MEG=1:0 to 0.001
EDA:organic by-products=1:0.0001 to 0.025.

Amount of Water:

Irrespective of whether the water-, EDA- and NMEDA-comprising mixture is used in the process of the invention directly after the removal of ammonia or indirectly after partial or complete removal of the higher-boiling amines, it is necessary in accordance with the invention for the proportion of water in the mixture to be at least as high as required for the formation of a high-boiling azeotrope with EDA at the appropriate bottom temperature.

In a particularly preferred embodiment, in the presence of one or more additional components in the mixture comprising EDA, NMEDA and H2O that form a high-boiling azeotrope with water, at least the amount of water that corresponds to the respective concentration of the respective one or more components that form a high-boiling azeotrope with water is additionally present.

More preferably, a distinct excess of water is present, such that all high-boiling azeotropes can be formed, while the excess of water is distilled off overhead.

Determination of the Azeotropic Composition

The determination of the composition of water and EDA at the azeotropic point of a binary mixture of water and EDA as a function of pressure is familiar to the person skilled in the art.

For instance, it is possible to experimentally measure azeotropic points as a function of pressure by methods known to those skilled in the art. Azeotropic points for the binary system of EDA and water can be found, for example, in the references cited in the book "Azeotropic Data Part I" (J. Gmehling, J. Menke, J. Krafczyk, K. Fischer, Wiley-VCH, 2004, page 425).

Moreover, the position of the binary mixture of EDA and water—i.e. a summary of the experimentally determined values—is likewise described in the relevant literature (see "Azeotropic Data Part I" by J. Gmehling, J. Menke, J. Krafczyk, K. Fischer, Wiley-VCH, 2004, page 425 or "Dortmund Data Bank" (http://www.ddbst.de/new/Default.htm).

The proportion by weight of water at the azeotropic point can also be calculated in a good approximation by activity coefficient models, such as NRTL. This method is implemented as standard in commercial simulation programs, such as Aspen Plus® from Aspentech. The abovementioned sources for mixture data also state calculation parameters, e.g. NRTL parameters, with the aid of which the azeotropic point can also be calculated at least in a good approximation for pressures different from the figures given.

Preferably, the proportion by weight of water at the azeotropic point is calculated by means of the NRTL model by Aspen. The calculation generally uses an ideal gas phase.

If the calculation uses a real gas phase, this is mentioned in the abovementioned sources for the mixture data. The vapor pressure curves for EDA and water can be found in the Dortmund Data Bank, other sources or other literature. It is thus possible to calculate the azeotropic point of EDA and water as a function of pressure.

The proportion by weight of water at the azeotropic point, which is calculated on the basis of models such as NRTL, can differ from the experimentally determined azeotropic composition within a certain error limit.

What is crucial for the calculation of the amount of water to be added is, however, the actual proportion by weight of water at the azeotropic point which occurs in reality.

In particular cases, there is no clear azeotrope, i.e. a clear value at which the curve which crosses the diagonal in a vapor-liquid equilibrium diagram of a binary mixture, and hence where the composition of the gas phase is identical to the composition of the liquid phase. In such cases, the x,y curve runs close to the diagonal and is barely distinguishable therefrom. In such cases, the amount of water must be sufficiently high that the curve can be seen to be above the diagonal at the corresponding concentration.

NMEDA Removal

The removal of NMEDA (NMEDA removal) from the mixtures which are obtained as described above, preferably by an EDA preparation process, ammonia removal and optionally a removal of the higher-boiling amines and optionally MEG and other high boilers, is effected in a rectification column (NMEDA removal column).

In the rectification column, a separation is generally effected into a low-boiling fraction comprising the major proportion of water and NMEDA, and a high-boiling fraction comprising the major proportion of EDA and any higher-boiling amines and any MEG if these have not already been partly or completely removed from the mixture beforehand.

Preferably, the bottom temperature in the rectification column is 155° C. or less, very preferably 145° C. or less and very especially preferably 140° C. or less.

Preferably, the bottom temperature is in the range from 50 to 155° C., more preferably in the range from 55 to 150° C., even more preferably in the range from 60 to 145° C. and especially preferably in the range from 75° C. to 140° C.

Surprisingly, the concentration of NMEDA in the output can be greatly reduced when the bottom temperature is within the preferred range. This is all the more surprising in that NMEDA and EDA are very similar components which are generally separable from one another only with difficulty.

The energy required for the evaporation is typically introduced by an evaporator in the bottom of the column. This evaporator is typically a natural circulation evaporator or forced circulation evaporator. Alternatively, it is possible to use evaporators with a short dwell time, falling-film evaporators, helical tube evaporators, wiped-film evaporators or a short-path evaporator.

If the rectification is conducted at a temperature of 155° C. or less, the proportion of NMEDA in the EDA end product can be drastically reduced.

This effect can be illustrated by FIG. 1, in which the amount of NMEDA in the bottoms is shown as a function of the bottom temperature. It can be inferred from FIG. 1 that the amount of NMEDA in the bottoms rises abruptly above 155° C.

The rectification temperature within the range of the invention is generally attained via establishment of a suitable pressure in the rectification.

Preference is given to choosing a minimum pressure for the rectification, more preferably one at which condensation of the vapor mixture obtained at the top under industrially customary conditions, i.e. a temperature at which condensation with cooling water or by cooling with ambient air is still possible. These are typically top temperatures of 20° C. or more, preferably 30° C. or more and more preferably 35° C. or more. The condensation is preferably effected within a temperature range from 20 to 60° C., preferably 30 to 55° C., more preferably 40 to 50° C.

If the input into the rectification column comprises essentially no higher-boiling amines, a pressure of 2.5 bar or less, preferably 1.6 bar or less and most preferably 1 bar or less should preferably be established at the top of the column. Such a low pressure additionally has the advantage that the complexity of separation in the rectification is reduced. Thus, it has been found in the context of this invention that the separation complexity for attainment of a qualitatively identical separation rises steeply above 1.6 bar, and an equivalent separation is no longer possible at pressures above 2.5 bar.

If the input into the rectification column comprises higher-boiling amines, it is generally necessary to lower the top pressure in order to attain the temperature according to the invention in the bottom of the column.

In a particularly preferred embodiment, the pressure at the top of the column is therefore preferably in the range from 5 to 800 mbar, more preferably in the range from 10 to 500 mbar, even more preferably in the range from 15 to 250 mbar and especially preferably 25 to 125 mbar.

The rectification can be effected in apparatuses known to those skilled in the art, such as bubble-cap tray columns, sieve tray columns or columns having random packings or structured packings. Preference is given to using internals with a low pressure drop, such as structured packings, for example in the form of sheet metal packing such as Mellapak 250 Y or Montz Pak (B1-250 type). It is also possible for a packing with lower or elevated specific surface area to be present, or it is possible to use a fabric packing or a packing with another geometry such as Mellapak 252.Y. What are advantageous about the use of these distillative internals are the low pressure drop and low specific liquid holdup compared to valve trays, for example. The internals may be disposed in one or more beds.

The rectification column preferably comprises 35 to 140 theoretical plates, more preferably 50 to 120 theoretical plates and most preferably 60 to 100 theoretical plates.

The input into the rectification column is preferably fed in in a spatial region between 25% and 95% of the theoretical plates of the rectification column (counted from the bottom), more preferably in a spatial region between 60% and 90% of the theoretical plates of the rectification column. For example, the feeding can be effected above the middle of the theoretical plates.

The low-boiling fraction comprising essentially water and NMEDA and possibly traces of EDA is preferably withdrawn in the upper region of the column, more preferably at the top of the column, and sent to a condenser. Condensers used may, for example, be condensers having cooling coils or helical tubes, jacketed tube condensers and shell and tube heat exchangers. To improve the removal of NMEDA, the condensate obtained in the condenser is preferably recycled into the top of the rectification column to an extent of more than 30%, preferably to an extent of more than 50%. The remainder is discharged from the process and generally sent to a collecting vessel and thence generally to a disposal, preferably a water treatment plant.

In the lower region of the column, a mixture comprising water, EDA and any higher-boiling amines and any MEG is generally drawn off. Preferably, the mixture is drawn off from the bottom of the column. In general, the bottoms comprise at least as much water as corresponds to the high-boiling water/EDA azeotrope, or somewhat more.

EDA Dewatering

The EDA-comprising bottom product from the NMEDA removal column is introduced into a second rectification column (EDA dewatering column).

In the EDA dewatering column, a separation is generally effected into a low-boiling fraction comprising the major proportion of water, and a high-boiling fraction comprising the major proportion of EDA and any higher-boiling amines and any MEG if these have not already been partly or completely removed from the mixture beforehand.

In a preferred embodiment, the pressure in the EDA dewatering column is adjusted such that the boiling point of the mixture obtained at the top is 10° C. or higher than the bottom temperature in the NMEDA removal column. Preferably, the boiling point of the mixture obtained at the top is 15° C. or higher, more preferably 20° C. or higher, very particularly 25° C. or higher and especially 30° C. or higher than the bottom temperature in the NMEDA removal column. In the context of the present invention, the boiling point of the mixture obtained at the top of the column is the temperature below which the mixture obtained at the top is in liquid form at the respective pressure at the top of the column. Since the mixture obtained at the top of the EDA dewatering column is generally a multicomponent mixture that may comprise not only water but also other components, the boiling point of the mixture obtained at the top is generally not identical to the dew point of the mixture. In the context of the present invention, the dew point of the mixture is the temperature at which the first amount of liquid condenses out of the gaseous mixture obtained at the top when heat is taken from the mixture and the temperature is reduced. Between the dew point and boiling point, the mixture is generally partly in the liquid phase and partly in the gas phase.

If the boiling temperature of the mixture obtained at the top of the EDA dewatering column is 10° C. or higher than the bottom temperature of the NMEDA removal column, the temperature differential between EDA dewatering column and NMEDA removal column is sufficiently great to be able to efficiently utilize the heat from the mixture obtained at the top of the EDA dewatering column for the operation of the NMEDA removal column.

In a preferred embodiment, the pressure in the rectification column is adjusted such that EDA and water do not form an azeotropic mixture. This is generally the case at a bottom temperature of 160° C. or more, preferably of 180° C. or more and especially preferably of 190° C. or more. When EDA and water do not form an azeotropic mixture, a particularly good separation of EDA and water can be achieved.

The energy required for the evaporation is typically introduced by an evaporator in the bottom of the column. This evaporator is typically a natural circulation evaporator or forced circulation evaporator. Alternatively, it is possible to use evaporators with a short dwell time, falling-film evaporators, helical tube evaporators, wiped-film evaporators or a short-path evaporator.

The rectification temperature is generally attained via establishment of a suitable pressure in the rectification.

In the preferred embodiment, therefore, the absolute pressure at the top of rectification column is 4 bar or more.

Preferably, the pressure at the top of the rectification column is in the range from 4 to 30 bar, more preferably 6 to 10 bar and especially preferably 7 to 9 bar.

The feed is more preferably in a spatial region between 50% and 100% of the theoretical plates of the rectification column. For example, the feed may be to the top of the column. The optimal feed point can be ascertained by the person skilled in the art with the customary calculation tools.

The number of theoretical plates is generally in the range from 10 to 80, preferably 30 to 60.

In the first embodiment of the invention, the EDA dewatering column has a condenser which is generally operated at a temperature at which the predominant portion of the water is condensed at the corresponding top pressure.

In general, the operating temperature of the condenser is in the range from 150 to 230° C., preferably 160 to 195° C.

Condensers used may, for example, be condensers having cooling coils or helical tubes, jacketed tube condensers and shell and tube heat exchangers.

A condensate comprising predominantly water is generally obtained in the condenser. Preferably, the condensate obtained in the condenser is recycled into the top of rectification column to an extent of more than 50%, preferably to an extent of more than 65%.

The unrecycled condensate can generally be sent directly to disposal, for example by introduction into a wastewater treatment plant.

In a further preferred embodiment, the condensate not recycled into the EDA dewatering is introduced into the bottom of the NMEDA removal column. This has the advantage that the amount of water in the NMEDA removal column is increased, and so the NMEDA removal column comprises as much water as required for the formation of a high-boiling azeotrope of EDA and water.

In the second embodiment of the invention, the vapors ("vapors" are understood here to mean the generally vaporous stream obtained at the top of a column before it is sent to a condenser) drawn off at the top of the EDA dewatering column are only partially condensed, if at all, and introduced into the NMEDA removal column. This embodiment is elucidated below.

At the top of the EDA dewatering column, a mixture comprising predominantly water is generally obtained.

The high-boiling output from the EDA dewatering column comprises essentially EDA and any higher-boiling amines and any MEG if the EDA is being prepared by the MEG preparation process.

Preferably, the high-boiling output comprises less than 1.0% by weight of water, preferably less than 0.6% by weight and more preferably less than 0.5% by weight of water.

This output can, as described below, be separated by the processes known to those skilled in the art into its individual components or suitable fractions in order to obtain, for example, on-spec EDA.

Purification of the EDA-Containing Outputs from the EDA Dewatering

Connection of the EDA Dewatering Column with the NMEDA Removal Column

Surprisingly, the energy requirement in the purification of EDA can be reduced when the thermal energy from the vapors that are drawn off at the top of the EDA dewatering column is utilized to make a contribution to the evaporation energy which is required in the NMEDA removal column.

The present invention therefore relates to a process for purifying ethylenediamine, in which a) a mixture comprising water (H2O), ethylenediamine (EDA) and N-methylethylenediamine (NMEDA) is introduced into a rectification column (NMEDA removal column), where the mixture introduced comprises at least the amount of water as required for the formation of a high-boiling azeotrope of EDA and water at the appropriate bottom temperature; and b) the EDA-comprising bottom product from the NMEDA removal column is introduced into a second rectification column (EDA dewatering column), which comprises (i) partly or fully condensing the vapors from the top of the EDA dewatering column in a condenser which is cooled with a medium which is at least partly evaporated during the condensation and the vapor thus formed is used at least partly to heat the evaporator of the NMEDA removal column; and/or (ii) introducing the vapors from the top of the EDA dewatering column into the NMEDA removal column.

The calculation of the amount of water in the mixture which is introduced into the NMEDA removal column as required for the formation of the high-boiling azeotrope of EDA and water at the appropriate bottom temperature is effected as described above.

Preferably, the temperature and pressure in the NMEDA removal column are chosen such that pressure and temperature are within the above-described preferred ranges.

Preferably, the bottom temperature in the rectification column is 155° C. or less, preferably 145° C. or less and most preferably 140° C. or less. Preferably, the bottom temperature is in the range from 50 to 155° C., more preferably in the range from 55 to 150° C., even more preferably in the range from 60 to 145° C. and especially preferably in the range from 75° C. to 140° C.

If the input into the rectification column comprises essentially no higher-boiling amines, a pressure of 2.5 bar or less, preferably 1.6 bar or less and most preferably 1 bar or less should preferably be established at the top of the column.

If the input into the rectification column comprises higher-boiling amines, the pressure at the top of the column is preferably in the range from 5 to 800 mbar, more preferably in the range from 10 to 500 mbar, even more preferably in the range from 15 to 250 mbar and especially preferably 25 to 125 mbar.

In a preferred embodiment, the boiling temperature of the mixture obtained at the top of the EDA dewatering column is 10° C. or higher than the bottom temperature in the NMEDA removal column. Preferably, the boiling point of the mixture obtained at the top is 15° C. or higher, more preferably 20° C. or higher, very particularly 25° C. or higher and especially 30° C. or higher than the bottom temperature in the NMEDA removal column.

In the context of the present invention, the boiling point of the mixture obtained at the top of the column is the temperature below which the mixture obtained at the top is in liquid form at the respective pressure at the top of the column. Since the mixture obtained at the top of the EDA dewatering column is generally a multicomponent mixture that may comprise not only water but also other components, the boiling point of the mixture obtained at the top is generally not identical to the dew point of the mixture. In the context of the present invention, the dew point of the mixture is the temperature at which the first amount of liquid condenses out of the gaseous mixture obtained at the top when heat is taken from the mixture and the temperature is reduced. Between the dew point and boiling point, the mixture is generally partly in the liquid phase and partly in the gas phase.

In order that the appropriate boiling temperature develops, it is preferable to choose the temperature and pressure in the EDA dewatering column such that pressure and temperature are within the above-described preferred ranges.

This is generally the case at a bottom temperature of 160° C. or more, preferably of 180° C. or more and especially preferably of 190° C. or more. In the preferred embodiment, therefore, the absolute pressure at the top of the rectification column is preferably 4 bar or more and is preferably in the range from 5 to 30 bar, more preferably 6 to 10 bar and especially preferably 7 to 9 bar.

In the first embodiment of the processes of the invention for purifying EDA, the vapors from the top of the EDA dewatering column are partly or fully condensed in a condenser connected to the top of the EDA dewatering column. The condensation is preferably effected as described above. The condenser is cooled with a medium which at least partly evaporates on condensation of the vapors that are drawn off at the top of the EDA dewatering column.

Since the operating temperature of the condenser, as described above, is generally in the range from 150 to 230° C., preferably 160 to 195° C., the material should be chosen correspondingly, such that it evaporates at the corresponding temperatures and the pressure that exists in the cooling spaces of the condenser.

The cooling medium used is more preferably water which, under the typical operating conditions of the condenser, evaporates at least partly, but preferably virtually completely, at the top of the EDA dewatering column.

The vapor formed in the evaporation of the cooling medium is at least partly used as heating vapor to heat the evaporator of the NMEDA column.

Evaporators which can be used in the NMEDA removal column have already been described above. In the evaporator of the NMEDA removal column, the vaporous cooling medium from the condenser of the EDA dewatering column releases some of its thermal energy to the bottom product from the NMEDA removal column which is supplied as feed. By virtue of the energy thus supplied, the bottom product, which generally has a lower evaporation temperature than the vaporous cooling medium from the EDA dewatering column, can at least partly evaporate. This has the advantage that the energy requirement of the primary evaporator of the NMEDA removal column can be reduced, which saves costs.

In the second embodiment of the processes of the invention for purifying EDA, the vapors from the top of the EDA dewatering column are partly or fully passed into the NMEDA removal column.

In this embodiment, the thermal energy from the vapors is utilized directly in order to make a contribution to the evaporation energy which is required in the NMEDA removal column. In order that the vapors can be passed partly or fully into the NMEDA removal column, the vapors are only partially condensed, if at all.

It is therefore preferable that the EDA dewatering column does not have a condenser.

When the EDA dewatering column has one or more condensers, in this preferred embodiment, these are operated in such a way that the vapors only partially condense, if at all. This can be effected, for example, in that the condenser at the top of the EDA dewatering column has an operating temperature corresponding at least to the condensation temperature of the vapors at the corresponding top pressure. Such a temperature can be achieved, for example, in that the condenser is cooled insufficiently, if at all.

The vapors from the EDA dewatering column that are drawn off from the top region are passed into the NMEDA removal column.

The introduction of the vapors into the NMEDA removal column comprises introduction into the column itself, for example as feed into the stripping section, preferably the bottom of the column, and introduction into an evaporator or heat exchanger which is connected to the NMEDA removal column and has the purpose of introducing heat into the NMEDA column for evaporation of the bottom product.

In a preferred embodiment of this second embodiment, the vapors are passed as heating vapor into a reboiler of the NMEDA removal column. In the evaporator, the vapors from the EDA dewatering column release some of their thermal energy to the bottom product from the NMEDA removal column which is supplied as feed. By virtue of the energy thus supplied, the bottom product, which generally has a lower evaporation temperature than the vapors from the EDA dewatering column, can at least partly evaporate. At the same time, the vapors supplied as heating vapor are partly or fully condensed in the evaporator. The condensate thus obtained can be sent to disposal, preferably a wastewater treatment, or introduced into the stripping section of the NMEDA removal column, preferably the bottom.

In a further preferred embodiment of this second embodiment, the vapors are introduced directly as feed into the stripping section of the NMEDA removal column. Preferably, the feed is into the bottom of the NMEDA removal column. Since the NMEDA removal column is generally operated at a lower pressure than the EDA dewatering column, it is advantageous when the vapors from the EDA dewatering column are throttled before they are introduced into the NMEDA removal column. The throttling of the vapors is preferably effected by suitable devices, for example throttle valves or control valves.

Since the vapors from the EDA dewatering column are generally at a significantly higher temperature than the bottom temperature of the NMEDA removal column, the vapors can be used for evaporation of the lower-boiling components in the column bottom of the NMEDA removal column, in that, as described above, they are either not condensed or only partially condensed and introduced directly into the NMEDA removal column, or in that they are utilized for evaporation of a coolant and the vaporous coolant is used as heat carrier.

The thermal utilization of the vapors from the EDA dewatering column can distinctly reduce the energy requirement of the evaporator in the NMEDA removal column, generally by the energy that would be obtained in the condensation of the vapors from the EDA dewatering column. This saves steam costs and power costs for operation of the evaporator of the NMEDA removal column, and also cooling water costs or operating costs for a condenser which is no longer present in the EDA dewatering column.

Figure 3:
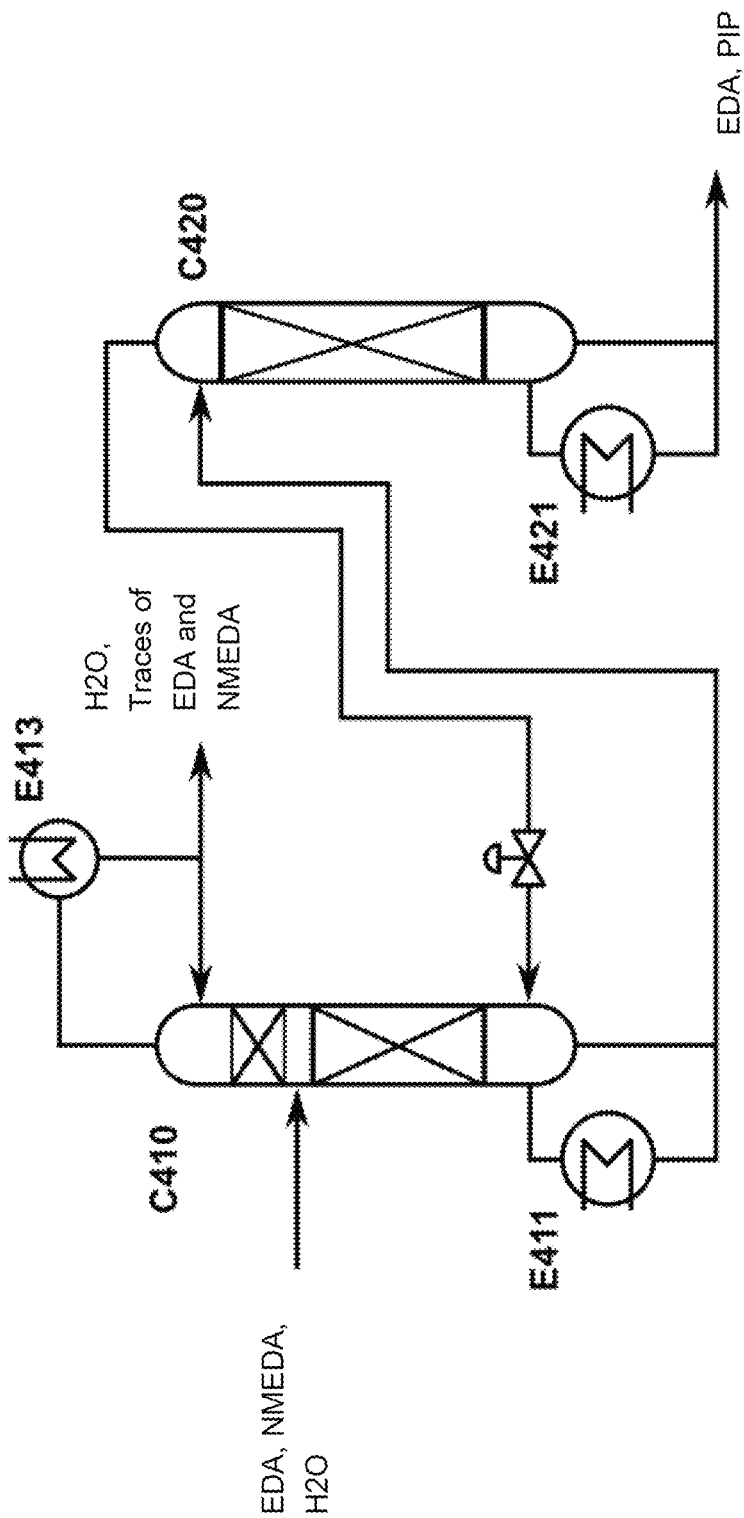
FIG. 3 illustrates the results from example 3. The column interconnection according to FIG. 3 differs from the interconnection according to FIG. 2 in that there is no condenser E423.

A preferred column interconnection of NMEDA removal column and EDA dewatering column is specified in FIG. 3.

In FIG. 3, a feed stream comprising water, NMEDA and EDA is introduced as feed into the middle region of the NMEDA removal column (C410). Column C410 has an evaporator at the bottom of the column (E411) and a condenser (E413) at the top of the column.

The NMEDA removal column is operated in such a way that a mixture of water, NMEDA and possibly small amounts of EDA is obtained in the condenser E413.

A portion of the condensate stream is discharged from the process, while the other portion is recycled as reflux into the top of the NMEDA removal column.

A mixture comprising water, EDA and higher-boiling amines is drawn off from the bottom of the NMEDA removal column (C410) and passed into the top region of the EDA dewatering column (C420).

The EDA dewatering column is operated in such a way that vapors comprising predominantly water are obtained at the top of the column, and a mixture comprising EDA, PIP and possibly higher-boiling amines is drawn off in the lower region of the column.

The vapors that are obtained at the top of the EDA dewatering column are passed directly, without prior condensation, into the bottom of the NMEDA removal column (C410).

Before being introduced into the NMEDA removal column, the vapors are throttled by a throttling device, for example a control valve, to the lower pressure that exists in the NMEDA removal column.

Since the vapors from the EDA dewatering have a higher temperature, for example 180 to 200° C., than the temperature in the bottom of the NMEDA removal column, the vapors (even after throttling) can introduce the energy required for evaporation of the low boilers present in the column bottom. This can reduce the energy input into the evaporator E411 of the NMEDA removal column.

EDA-PIP Removal

When the high-boiling output from the EDA dewatering column comprises both EDA and higher-boiling amines, with or without MEG, there is generally first a separation into a lower-boiling fraction comprising PIP and EDA, and a higher-boiling fraction generally comprising the higher-boiling amines than PIP and any MEG. This separation can likewise be conducted in the rectification column (EDA-PIP removal). The exact operating conditions of the rectification column can, in accordance with the separation performance of the column used, be determined in a routine manner by the person skilled in the art by customary calculation methods using the known vapor pressures and evaporation equilibria of the components introduced into the rectification column. For example, the EDA-PIP removal can be conducted as described in EP 2 507 202 or in the aforementioned IPRP Report, page 89 et seq. in conjunction with FIG. 6.1, to which reference is hereby made explicitly.

The higher-boiling fraction is preferably drawn off at the bottom of the rectification column and generally comprises the higher-boiling amines.

The higher-boiling amines can be separated into the pure substances or suitable fractions by means of customary methods, especially by rectification. The workup of the higher-boiling amines is likewise described in the aforementioned PRP Report, page 89 et seq. in conjunction with FIG. 6.1 or EP 2487151, EP2507202 or EP2346809.

The lower-boiling fraction which is preferably drawn off in the upper region of the columns typically comprises EDA and PIP and is generally predominantly free of other higher-boiling amines. The proportion of higher-boiling amines (excluding piperazine) is generally less than 0.2% by weight, preferably less than 0.1% by weight and more preferably less than 0.05% by weight. In order to obtain on-spec EDA, the low-boiling EDA-PIP fraction is generally sent to a further purification stage (purifying EDA distillation).

Purifying EDA Distillation

The low-boiling fraction from the EDA/PIP removal is typically introduced into a further rectification column (purifying EDA distillation) which is preferably operated in such a way that EDA is obtained at the top of the column and piperazine can be drawn off at the bottom of the column. The exact operating conditions of the rectification column can, in accordance with the separation performance of the column used, be determined in a routine manner by the person skilled in the art by customary calculation methods using the known vapor pressures and evaporation equilibria of the components introduced into the rectification column. For example, the EDA-PIP removal can be conducted as described in EP 2 507 202 or in the aforementioned PRP Report, page 89 et seq. and FIG. 6.1, to which reference is hereby made explicitly.

In the condenser, a condensate comprising predominantly EDA but only very small amounts of NMEDA is generally obtained.

The low-boiling EDA-comprising fraction thus obtained is generally predominantly free of higher-boiling amines, including piperazine. The proportion of higher-boiling amines, including piperazine, is generally less than 0.5% by weight, preferably less than 0.3% by weight and more preferably less than 0.2% by weight.

In addition, the low-boiling EDA-comprising fraction preferably comprises 99.5% by weight or more of EDA.

The concentration of NMEDA in the EDA-containing fraction is preferably in the range from 0.001% to 0.1% by weight, preferably 0.005% to 0.08% by weight and more preferably in the range from 0.01% to 0.05% by weight.

Preferred Combinations

The above-detailed process steps and the respective embodiments of the individual process steps can be combined with one another in a suitable manner, and so the present invention also encompasses suitable combinations of the above-detailed process steps and the respective embodiments.

More particularly, the following combinations are preferred:

Combination of an EDA preparation process which is an EDA process with an ammonia removal, an NMEDA removal, an EDA dewatering, an EDA-PIP removal and a purifying EDA distillation.

Combination of an EDA preparation process which is an MEG process with an ammonia removal, an NMEDA removal, an EDA dewatering, an EDA-PIP removal and a purifying EDA distillation.

Combination of an EDA preparation process which is a C1 process with an ammonia removal, an NMEDA removal, an EDA dewatering, an EDA-PIP removal and a purifying EDA distillation.

Combination of an EDA preparation process which is an EDC process with an ammonia removal, an NMEDA removal, an EDA dewatering, an EDA-PIP removal and a purifying EDA distillation.

More particularly, preference is given to those of the aforementioned combinations in which the respective process steps themselves, for example the NMEDA removal and the EDA dewatering and the energetically advantageous interconnections thereof are executed in the respective preferred embodiments.

Advantages and Applications

EDA which has been obtained after the purifying EDA distillation or after the azeotropic removal of water is advantageously suitable for applications where very high purity of the EDA is important.

The EDA thus obtained can be used, for example, for preparation of high molecular weight polymers such as polyamides, since the functionality of the EDA is not reduced by the formation of NMEDA. For example, the EDA thus obtained can also be used as an electronics chemical or as a high-purity chemical for use in the field of crop protection agents, pesticides, epoxy resins, complexing agents, or for applications in the leather industry, the paper industry or the detergents industry. The use of high-purity chemicals increases the yield of end product, reduces the concentration of unwanted by-products and can also lead to an improvement in the use and processing properties in the fields of use in question. For instance, NMEDA, in polycondensation reactions, for example in the preparation of epoxy resins or polyamides, can lead to unwanted chain termination reactions which can reduce the degree of polymerization or the density at network points.

The process of the invention has the advantage that the separation complexity and energy expenditure in the rectification is reduced.

By means of the process of the invention for removing NMEDA from a mixture comprising EDA, NMEDA and water which is obtained in the preparation of EDA, it is additionally possible to obtain an on-spec EDA having a content of at least 99.5% by weight of EDA and an NMEDA content of 1000 ppm by weight or less even when greater amounts of NMEDA form in the preparation of EDA. This may be the case, for example, when EDA is prepared from C1 units, such as formaldehyde and hydrogen cyanide, or when catalysts show partial deactivation with increasing operating time and the reaction temperature has to be increased to compensate for the deactivation. The increase in the temperature generally results in a deterioration in selectivity in relation to the preparation of EDA, and increased formation of NMEDA as by-product. Thus, the process of the invention also enables an increase in the periods of use of catalysts in the preparation of EDA.

By means of the process of the invention, it is thus possible to obtain a high-purity EDA that can be used as starting material in a multitude of applications with increased yields and fewer side reactions.

The process of the invention is elucidated by examples which follow.

EXAMPLE 1

In the example which follows, a batchwise rectification column with one hundred theoretical plates (provided with a commercial packing of low pressure drop) was put under complete reflux (in batchwise mode). The vapor load on the column was adjusted via choice of a suitable diameter such that the pressure drop between the bottom and top was less than 5% of the top pressure established, such that the effect of the pressure on the boiling temperature of the mixture across the column played only a minor role. By simultaneous sampling at the top and bottom, the NMEDA content and water content were determined. The profile of the column was adjusted by variation of the column profile (adjustment of the masses by raising or lowering the liquid level in the distillate vessel or in the bottom) such that 100 ppm by weight of EDA were present at the top. The rest was water, with or without NMEDA. The amount of NMEDA in the starting mixture was chosen such that it was 1000 ppm by weight based on the amount of EDA. The amount of water was 75% of the amount of EDA by mass (75 kg of water, 100 kg of EDA). The starting mixture was initially charged in the bottom, and the column was brought to the boil by heating the bottoms with complete reflux. After a wait time of at least one hour, the samples were taken, such that it was ensured that the column profile was at a steady state.

The results are shown as a graph in FIG. 1.

In FIG. 1, the solid curve represents the NMEDA concentration in the bottoms (to be read off on the right-hand ordinate), and the dotted curve the water concentration in the bottoms (to be read off on the left-hand ordinate). The dashed-and-dotted curve represents the top pressure of the column (to be read off on the left-hand ordinate). The crosses represent the measurement points.

It is clearly apparent that, up to a bottom temperature of 140° C., the mixture in the bottoms from the column is virtually NMEDA-free, meaning that all NMEDA in the original mixture is present together with the residual water at the top, with virtually all EDA in the form of a high-boiling azeotrope with water in the bottoms (the dotted curve represents the composition of the high-boiling water/EDA azeotrope as a function of temperature). Above 140° C., enrichment of NMEDA in the bottoms commences, meaning that it is less easily separable from the EDA. At about 155° C., only half of the NMEDA can be removed overhead. Above 170° C., the majority of the NMEDA is in the bottoms with the EDA, i.e. is barely removable. The stated water concentration in the bottoms corresponds to the high-boiling water/EDA azeotrope at the respective temperature.

Thus, example 1 shows that, in the preferred embodiment of the present invention in which the bottom temperature in the NMEDA removal column is 155° C. or less, it is possible to achieve a particularly high quality of EDA.

EXAMPLE 2

Figure 2:
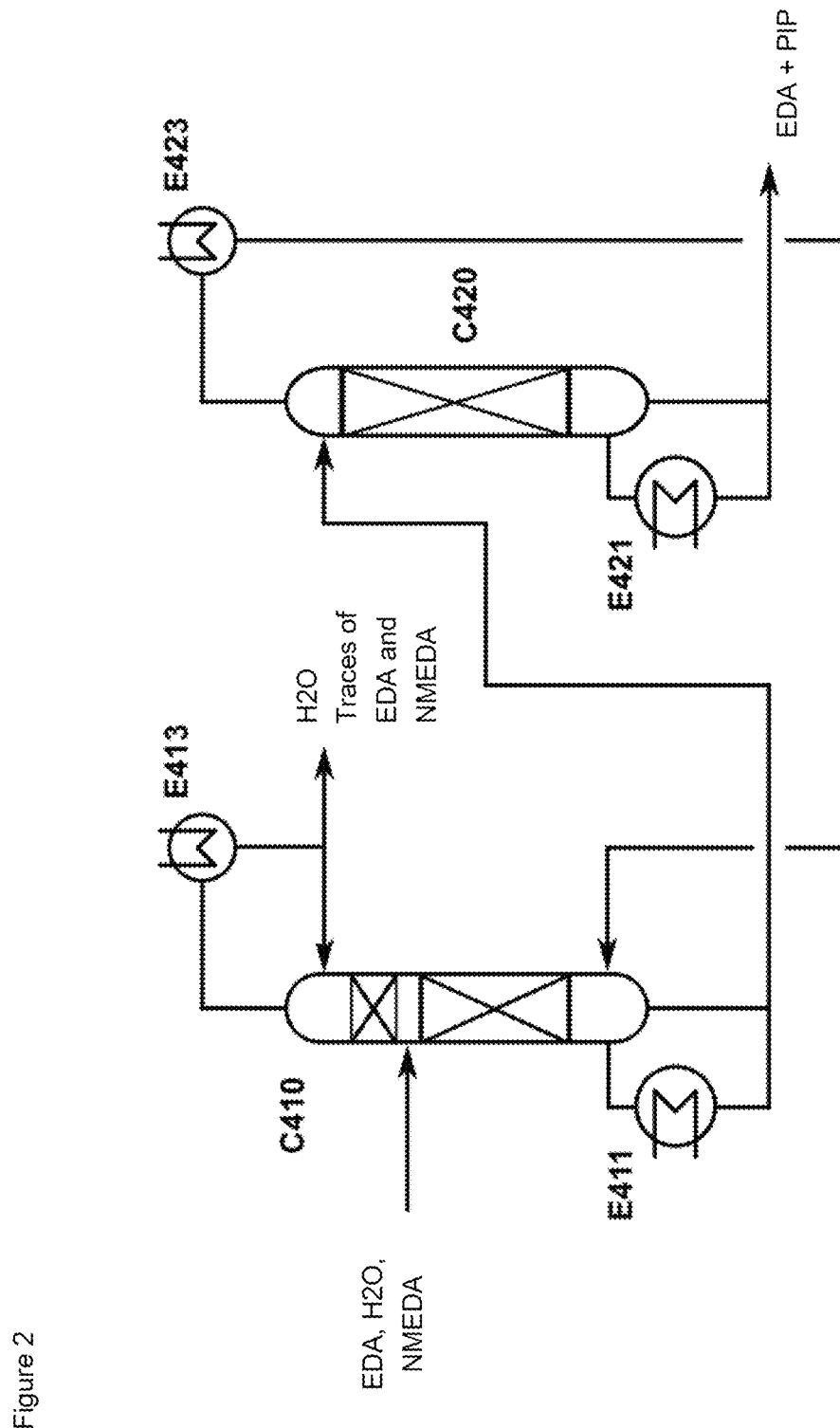
FIG. 2 illustrates the results from example 2.

In a column interconnection according to FIG. 2, a mixture comprising 3420 kg/h of water, 4 kg/h of NMEDA and 4160 kg/h of EDA was worked up in a first column at a top pressure of 150 mbar such that the EDA product (at the bottom of the second column C420) comprised only 1 ppm of NMEDA. For this purpose, a stripping section having 67 theoretical plates and a rectifying section having 13 theoretical plates are required at a reflux rate of 6.2 t/h. The water removed overhead comprises 100 ppm of EDA and virtually all the NMEDA from the feed mixture. In the evaporator E411, 4.7 MW have to be transferred. The bottoms output from C410 is worked up in a further column C420 at a top pressure of 8.5 bar such that the product at the bottom comprises only 0.4% water. A further reduction in the water content is possible when the column pressure and hence the bottom temperature is increased. In this example, C420 comprises a stripping section only. The vapors from C420 are condensed in the condenser E423. The condensate, consisting of a mixture of EDA and water, is recycled to C410. The power demand of evaporator E421 is 4.1 MW. In the condenser E423, 2.9 MW have to be removed.

EXAMPLE 3

An experiment analogous to example 2 was conducted in a column interconnection according to FIG. 3. The column interconnection according to FIG. 3 differs from the interconnection according to FIG. 2 in that there is no condenser E423. The vapors from C420 are introduced into the bottom of C410 without being condensed. Thus, no cooling output is required at the top of C420. The power demand of the evaporator E411 declines as a result of the interconnection of the invention from 4.7 MW to 1.8 MW, which corresponds to a distinct energy saving.

EXAMPLE 4

Figure 4:
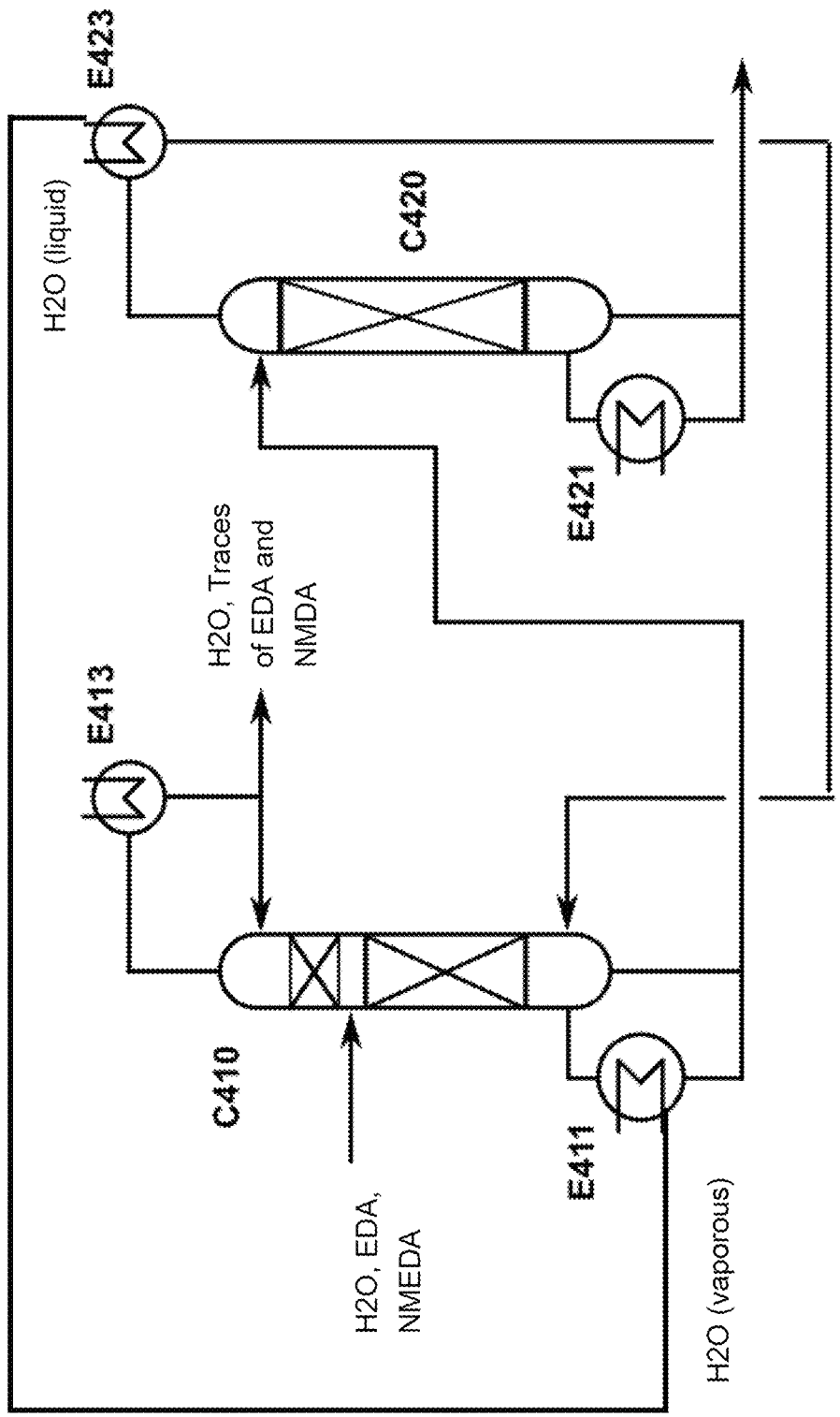
FIG. 4 illustrates the results from example 4. The column interconnection according to FIG. 4 differs from the interconnection according to FIG. 2 in that the water coolant is evaporated in the condenser E423 and the vaporous coolant is used to heat the evaporator of the NMEDA removal column.

An experiment analogous to example 2 was conducted in a column interconnection according to FIG. 4. The column interconnection according to FIG. 3 differs from the interconnection according to FIG. 2 in that the water coolant is evaporated in the condenser E423 and the vaporous coolant is used to heat the evaporator of the NMEDA removal column. The power demand of evaporator E411 can be considerably reduced compared to the interconnection according to FIG. 2.

The invention claimed is:

1. A process for purifying ethylenediamine, in which
   a) a mixture comprising water (H2O), ethylenediamine (EDA) and N-methylethylenediamine (NMEDA) is introduced into a rectification column (NMEDA removal column), where
   the mixture introduced comprises at least the amount of water as required for the formation of a high-boiling azeotrope of EDA and water at the appropriate bottom temperature; and
   b) the EDA-comprising bottom product from the NMEDA removal column is introduced into a second rectification column (EDA dewatering column),
   which comprises (i) partly or fully condensing the vapors from the top of the EDA dewatering column in a condenser which is cooled with a medium which is at least partly evaporated during the condensation and the vapor thus formed is used at least partly to heat the evaporator of the NMEDA removal column; and/or (ii) introducing the vapors from the top of the EDA dewatering column into the NMEDA removal column.

2. The process according to claim 1, wherein the pressure at the top of the EDA dewatering column is adjusted such that the boiling temperature of the mixture obtained at the top is 10° C. or higher than the bottom temperature of the NMEDA removal column.

3. The process according to claim 1, wherein the pressure at the top of the NMEDA removal column is 2.5 bar or less and the pressure at the top of the EDA dewatering column is 4 bar or more.

4. The process according to claim 1, wherein the pressure at the top of the NMEDA removal column is in the range from 25 to 200 mbar.

5. The process according to claim 1, wherein the NMEDA removal column is operated at a bottom temperature $T_S$ of 155° C. or less.

6. The process according to claim 1, wherein the EDA dewatering column is operated at a bottom temperature of 180° C. or more.

7. The process according to claim 1, wherein, in alternative (i) of claim 1, the condenser is operated at a temperature in the range of 150-230° C.

8. The process according to claim 1, wherein, in alternative (i) of claim 1, the cooling medium is water.

9. The process according to claim 1, wherein the vapors introduced into the NMEDA removal column from the top of the EDA dewatering column are only partially condensed, if at all.

10. The process according to claim 9, wherein the EDA dewatering column does not have a condenser or the condenser at the top of the EDA dewatering column is operated such that the vapors only partially condense, if at all.

11. The process according to claim 9, wherein the vapors from the EDA dewatering column are introduced as heating vapor into a reboiler of the NMEDA removal column.

12. The process according to claim 9, wherein the vapors from the EDA dewatering column are introduced into the stripping section of the NMEDA removal column.

13. The process according to claim 9, wherein the vapors from the EDA dewatering column are introduced into the bottom of the NMEDA removal column.

14. The process according to claim 12, wherein the vapors from the EDA dewatering column are throttled before being introduced into the NMEDA removal column in that the vapors are guided through an expansion valve or throttle valves.

15. The process according to claim 1, wherein the bottom product from the EDA dewatering column in step b is sent to a workup in which EDA and piperazine (PIP) are first separated from the higher-boiling amines in a rectification column and a further rectification column EDA is separated from PIP.

* * * * *